United States Patent
Hassan et al.

(10) Patent No.: US 6,465,220 B1
(45) Date of Patent: Oct. 15, 2002

(54) GLYCOSYLATION USING GALNAC-T4 TRANSFERASE

(75) Inventors: Frau Helle Hassan, Frederiksberg; Henrik Clausen, Holte; Eric Paul Bennett, Lyngby, all of (DK); Detlef Eisenkrätzer, Lörrach; Jochen Gätgens, Jülich, both of (DE)

(73) Assignee: GlycoZym ApS, Holte (DK)

( * ) Notice: Subject to any disclaimer, the term of this patent is extended or adjusted under 35 U.S.C. 154(b) by 0 days.

(21) Appl. No.: 09/217,306

(22) Filed: Dec. 21, 1998

(51) Int. Cl.$^7$ .............................. C12P 19/18; C12P 1/00; C12P 21/06; C12P 19/00; C12P 9/10
(52) U.S. Cl. .............................. 435/97; 435/41; 435/72; 435/183; 435/68.1; 435/193
(58) Field of Search .......................... 424/277.1, 279.1, 424/280.1; 530/350; 435/68.1, 72, 97; 514/25; 536/4.1, 17.2, 17.9, 18.7

(56) References Cited

PUBLICATIONS

Kumar et al. Core–2 beta–1–6N– acetylglucosaminyltransferase enzyme activity is critical for P–selectin glycoprotein ligand 1 binding to P–selectin, Blood, No. 15, 1996, vol. 88(10):3872–3879.*

Hagen et al. cDNA cloning and expression of a novel UDP–N–acetyl–D–galactosamine:polypeptide N–acetylgalactosaminyltransferase. J. Biol. Chem., vol. 272(21): 13843–13848, May 1997.*

GenBank Accession No. O08832, Hagen et al. Polypeptide GalNac Transferase–T4, Jan. 7, 1997, May 1997.*

Nishimore et al. N–galactosamine glycosylation of MUC–1 tandem repeat peptides by pancreatic tumor cell extracts. Cancer Research 54:3738–3744. (1994).*

Liu et al. Identification of N–terminal residues on P–selectin glycoprotein ligand–1 required for binding to P–selectin. Journal of Biological Chemistry 273:7078–7087. (1998).*

Wandall et al. Substrate specificities of three members of the human . . . GalNAc–T1, –T2 and –T3. Journal of Biological Chemistry. 272:23503–23514. (1997).*

Bennett UDP–GalNAc:polypeptide N–acetylgalactosyaminyltransferase T –4. EMBL Database accession No. YO8564; E307951. Jul. 1997.*

The Journal of Biological Chemistry, vol. 273, 1998 "Cloning of a Human UDP–N–Acetyl . . . MuC1 Tandem Repeat", Bennett et al., pp. 30472–30481.

The Journal of Biological Chemistry, vol. 272, 1997 "cDNA Cloning and Expression of a Novel . . . Acetylgalatosaminyltransferase" Hagen et al., pp. 13843–13848.

Glycobiology, vol. 6, 1996, "A family of UDP–GalNac: polypeptide . . . muclain–type O–linked glycosylation", Clausen et al., pp. 635–646.

\* cited by examiner

Primary Examiner—Rebecca E. Prouty
Assistant Examiner—Manjunath Rao
(74) Attorney, Agent, or Firm—Connolly Bove Lodge & Hutz LLP

(57) ABSTRACT

The use of human polypeptide N-acetylgalactosaminytransferase T-4 (GalNAc-T4) to glycosylate substrates is disclosed. The action of GalNAc-T4 can complement the activities of GalNAc-T1, -T2 and -T3. The glycosylated substrates are useful in preparation of vaccines and anti-inflammatory agents. A method of producing the soluble form of the enzyme is also disclosed.

4 Claims, 1 Drawing Sheet

GLYCOSYLATION USING GALNAC-T4 TRANSFERASE

FIELD OF THE INVENTION

The invention concerns protein glycosylation, and in particular, the glycosylation of protein or polypeptide substrates using human or animal GalNAc-T4 transferase. In another aspect, the invention concerns the generation and high-level secreted expression of glycosyltransferase enzymes, and other transmembrane proteins, in mammalian host cells.

BACKGROUND AND PRIOR ART

Glycosylation is the addition of glycan moieties to proteins. The initial steps of glycosylation involve recognition events between protein and a glycosyltransferase, which events determine the sites of glycan attachment. Different glycosyltransferases have been isolated and identified, and a number of specific sites of glycan addition to proteins have been determined.

The glycosylation of serine and threonine residues during mucin-type O-linked protein glycosylation is catalyzed by a family of polypeptide GalNAc transferases (EC 2.4.1.41). Five distinct GalNAc-transferase genes termed GalNAc-T1, -T2, -T3, -T4 and -T5 have been cloned and characterized. Homa et al., J. Biol. Chem. 268:12609 (1993); Hagen et al., J. Biol. Chem. 273:8268 (1998); White et al., J. Biol. Chem.270: 24156 (1995); Bennett et al., J. Biol. Chem. 271:17006 (1996); Bennett et al., Glycobiology 8:547 (1998); Hagen et al., J. Biol. Chem. 272:13843 (1997); Hagen et al., J. Biol. Chem. 273:27749 (1998). The GalNAc transferases characterized to date have distinct acceptor substrate specificities. Bennett et al. (1996), supra; Wandall et al., J. Biol. Chem. 272:23503 (1997); Bennett et al. (1998), supra. Recent findings have suggested that the GalNAc-transferases comprise a gene family and that each GalNAc transferase has distinct functions.

Isolation of GalNAc-T3 and use of the GalNAc-T3 polypeptide to glycosylate substrates are disclosed in copending application Ser. No. 648,298, filed May 15, 1996, the disclosure of which is incorporated by reference.

A putative murine orthologue of GalNAc-T4 is described in Hagen et al., J. Biol. Chem. 272:13843 (1997). The murine GalNAc-T4 was tested with a small panel of peptides, including two sequences from the tandem repeat of MUC1, and no activity with those substrates was found in that study. O-glycosylation of the cancer-associated cell membrane mucin, MUC1, has attracted attention because it is altered in cancer cells with smaller and fewer glycans. Taylor-Papadimitriou et al., Ann. N.Y. Acad. Sci. 690:69 (1993); Lloyd et al., J. Biol. Chem. 271:33325 (1996); Brockhausen, Eur. J. Biochem. 233:607 (1995). The change in O-glycosylation leads to exposure of cancer-associated epitopes within the tandem repeat region of MUC1. Analysis of the in vitro O-glycosylation properties of various GalNAc-transferase preparations, including purified GalNAc-T1, GalNAc-T2 and GalNAc-T3 suggests that only three of five possible sites in the repeat are glycosylated. Wandall et al. (1997), supra.

The cell adhesion molecule, P-selection, binds to its ligand, the P-selection glycoprotein ligand 1 (PSGL-1) through interaction with an O-glycan at threonine 57. Liu et al., J. Biol. Chem. 273:7078 (1998). Previous unpublished findings have suggested that GalNAc-T1, GalNAc-T2 and GalNAc-T3 do not utilize this substrate.

SUMMARY OF THE INVENTION

The use of GalNAc-T4 is disclosed for the O-glycosylation of substrates. It has been found that GalNAc-T4 exhibits a different substrate specificity than previously-characterized GalNAc-transferases.

The unique specificity of human GalNAc-T4 is exemplified by its ability to glycosylate specific serine and threonine residues in MUC1 tandem repeat and PSGL-1. For example, GalNAc-T4 glycosylates two sites in the MUC1 tandem repeat sequence using MUC1 tandem derived glycopeptides. Further characterizing the unique activity of GalNAc-T4 is its ability to glycosylate synthetic peptides derived from PSGL-1.

In a preferred embodiment, a method of glycosylation is disclosed which comprises glycosylation of substrates with GalNAc-T4, used in combination with GalNAc-T1, GalNAc-T2 and/or GalNAc-T3.

Substrates which are glycosylated in accordance with the method of the present invention are useful for the preparation of glycoprotein-based vaccines and anti-inflammatory agents.

In a related method, soluble GalNAc-T4, or soluble forms of other type II transmembrane proteins, are produced and detected in animal cells with high-level expression. In this embodiment, a truncated form of the protein, which excludes the N-terminal hydrophobic signal sequence, is provided in association with a suitable secretion signal, SEQ ID NO:10. Host cells expressing the soluble form of protein are detected by screening with an antibody raised against the soluble form of the protein.

DESCRIPTION OF THE PREFERRED EMBODIMENTS

Figure 1:
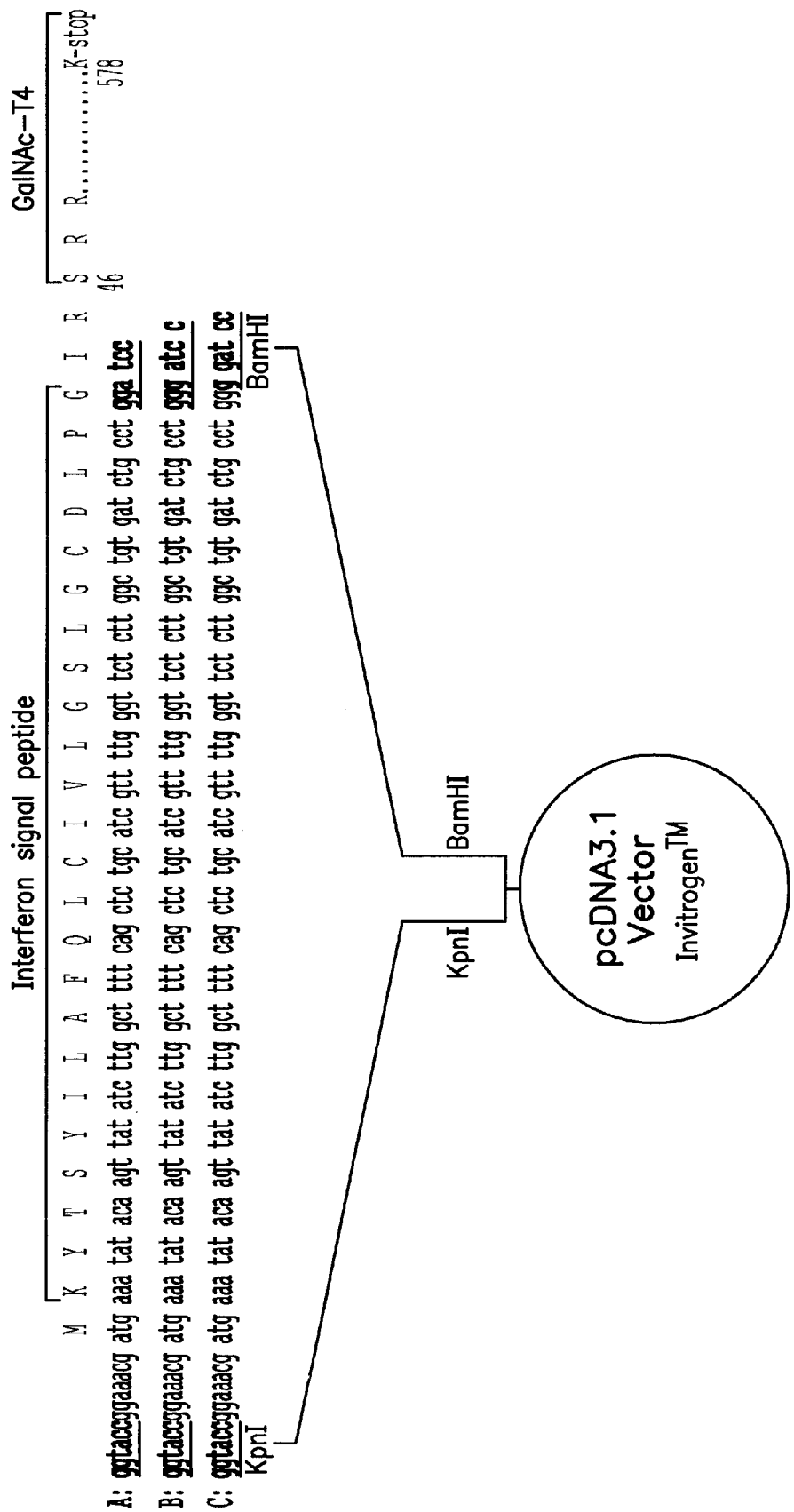
FIG. 1 is a diagram showing certain sequences (SEQ. ID NOs:11 through 13) of the cloning vector and the predicted sequence of the amino acid translation (SEQ ID NO:10) used in Example 2.

The N-acetylgalactosaminyltransferase T4 (GalNAc-T4) gene has been isolated from a human salivary gland library as described in Bennett et al., J. Biol. Chem. 273:46 (1998).

The sequence of the GalNAc-T4 nucleic acid so isolated is shown in SEQ ID NO:1. This sequence has been submitted to GenBank/EBI Data Bank and assigned accession number Y08564.

The sequence of the encoded GalNAc-T4 polypeptide is shown in SEQ ID NO:2.

Expression to produce enzymatically-active GalNAc-T4 can be carried out in any number of conventional expression systems familiar to those skilled in the art. In one embodiment, GalNAc-T4 is expressed in a soluble form which can be recovered from the culture medium. In another embodiment, host cells (e.g. CHO cells) are engineered to express GalNAc-T4 and glycosylate substrates in vivo in host cells. Expression in CHO cells is currently preferred.

In accordance with one embodiment of the method of the invention, enzymatically active human GalNAc-T4 is contacted with an acceptor substrate and an N-acetylgalactosamine donor substrate, preferably UDP-N-acetylgalactosamine, under conditions for transfer of N-acetylgalactosamine from the donor substrate to the acceptor substrate. Glycosylated acceptor substrate is then obtained. Preferred substrates are proteins and peptides.

Particularly preferred substrates are MUC1 tandem repeat, PSGL-1, and/or portions or multimers of those molecules. Transfer assays for carrying out glycosylation are familiar to those in the art, and are described in the literature cited above and in the examples provided below.

As noted, human GalNAc-T4 demonstrates a unique acceptor substrate specificity. GalNAc-T4 has been found to transfer GalNAc to two sites in the MUC-1 tandem repeat sequence: Ser in GVTSA and Thr in PDTR using a 24-mer glycopeptide with GalNAc residues attached at sites utilized by GalNAc-T1, -T2 and T3 (TAPPAHGVTSAPDTRPAPG STAPPA, SEQ ID NO:3, wherein the GalNAc sites are underlined). In an important aspect of the invention, the action of GalNAc-T4 can be used to complement the action of other GalNAc-transferases in the O-glycosylation of MUC1. In particular, glycosylation of substrate using GalNAc-T4 can be carried out in combination with (e.g. during or after) glycosylation using GalNAc-T1, -T2 and/or T3. A most preferred substrate in accordance with the invention has been previously glycosylated, at one or more sites, by GalNAc-T1, -T2 or -T3, or another GalNAc-transferase.

As noted, GalNAc-T4 can be produced in any desired expression system. Among the various means for expressing enzymatically active protein, a currently preferred embodiment comprises providing a vector encoding a truncated form of the protein, which excludes the N-terminal hydrophobic signal sequence, is provided in association with a suitable secretion signal. Host cells expressing the soluble form of protein are detected by screening with an antibody raised against the soluble form of the protein.

This embodiment is applicable not only to GalNAcT4, but to other glycosyltransferases and other type II transmembrane proteins, which can be produced using these same steps.

Preferably, the secretion signal is an interferon secretion signal, most preferably a gamma-interferon signal. The secretion signal sequence is provided in an expression vector to be expressed with the truncated form of the glycosyltransferase so as to direct the secretion of the glycosyltransferase.

Preferred host cells are Chinese Hamster Ovary (CHO) cells.

Antibodies against the soluble forms of the glycosyltransferase enzymes are raised using conventional methods. Preferably the screening antibody is a monoclonal antibody.

The use of this expression/screening strategy allows high-expressing cells to be identified by staining. Cells stained strongly in the cytoplasm and/or culture medium can be identifed as high-level producers of the soluble enzyme. Large panels of transfectant cells can be screened for activity by simply making duplicate clones of the producing cells (e.g. on a cover slip) and reacting the clones with the antibody. This is much more efficient and expedient than use of an activity-based assay to identify high-producing clones. The method can also be preferable to FACS sorting, which may not be as effective for identification of high-level producers of intracellular proteins destined for secretion.

The following examples are provided to illustrate certain preferred embodiments of the invention, and should be considered as illustration and not as limitation. In the examples, GalNAc-transferase assays were performed in 50 $\mu$l total reaction mixtures containing 25 mM cacodylate (pH 7.5), 10 mM $MnCl_2$, 0.1–0.25% Triton X-100, 150–200 $\mu$M UDP-[$^{14}$C]-GalNAc (4,000 cpm/nmole) (Amersham) and 0.06–1 mM acceptor peptides. Peptides were either synthesized or obtained from Carlbiotech (Copenhagen), or Neosystems (Strasbourg), and quality was ascertained by amino acid analysis and mass spectrometry. Peptides Muc-1a, Muc-1b, and TAP24, were derived from the tandem repeat of human MUC1, Gendler et al., J. Biol. Chem. 265:15286 (1990), and Muc2, Muc5AC, and Muc7 from the tandem repeats of MUC2, MUC5AC, and MUC7, respectively. Gum et al., J. Biol. Chem. 264:6480 (1989); Porchet et al., Biochem. Soc. Trans. 23:800 (1995); Bobek et al., J. Biol. Chem. 268:20563 (1993). GalNAc$_4$TAP24 was produced by in vitro glycosylation using GalNAc-T2 as described in Wandall et al., J. Biol. Chem. 272:23503 (1997). Products were quantified by scintillation counting after chromatography on Dowex-1, octadecyl silica cartridges (Bakerbond), or HPLC (PC3.2/3 or mRPC C2/C18 SC2.1/10 Pharmacia, Smart System). Products produced by in vitro glycosylation were in most cases also confirmed by mass spectrometry.

Mass spectra were acquired on either Voyager-DE or Voyager-Elite MALDI time-of flight mass spectrometers (Perseptive Biosystem Inc.), equipped with delay extraction. The MALDI matrix was a 9:1 mixture of 2,5-Dihydroxybenzoic acid (2,5-DHB) 25 g/l and 2-hydroxy-5-methoxy benzoic acid 25 g/l (Aldrich) dissolved in a 2:1 mixture of 0.1% trifluoroacetic acid (TFA) in water and acetonitrile. Samples dissolved in 0.1% TFA to a concentration of approximately 2 pmol/ml were prepared for analysis by placing 1 $\mu$l of sample solution on a probe tip followed by 1 $\mu$l of matrix.

EXAMPLE 1

In this example, GalNAc-T4 was expressed in Sf9 insect cells. Expression constructs designed to contain amino acid residues 32-578 of the coding sequence of the putative GalNAc-T4 gene shown in SEQ ID NO:1 prepared by genomic PCR of two clones containing GalNAc-T4 (described in Bennett et al. (1998), supra) were cloned into a BamHI site of the expression vector pAcGP67 (Pharmingen), and the expression construct was sequenced. The constructs pAcGP67-GalNAc-T4$_{506V}$sol and pAcGP67-GalNAc-T4$_{506}$ I sol, were designed to yield a putative soluble form of the GalNAc-T4 protein with an N-terminal end positioned immediately C-terminal to a potential transmembrane domain and including the entire sequence expected to contain the catalytic domain. Control constructs pAcGP67-GalNAc-T1-sol, pAcGP67-GalNAc-T2-sol, pAcGP67-GalNAc-T3-sol, and pAcGP67-O$^2$-sol were prepared as previously described in White et al., J. Biol. Chem 270:24156 (1995); Bennett et al., J. Biol. Chem. 271:17006 (1996); and Bennett et al., Biochem. Biophys. Res. Comm. 211:347 (1995).

A full coding expression construct was prepared by PCR and cloned into BamHI sites of the expression vector pVL1392 (Pharmingen). Co-transfection of Sf9 cells with pAcGP67-constructs or pVL-constructs and Baculo-Gold™ DNA was performed according to the manufacturer's specifications. Briefly, 0.4 $\mu$g construct was mixed with 0.1 $\mu$g Baculo-Gold DNA and co-transfected in Sf9 cells in 24-well plates. Ninety-six hours post-transfection, recombinant virus was amplified in 6-well plates at dilutions of 1:10 and 1:50. Titer of amplified virus was estimated by titration in 24-well plates with monitoring of GalNAc-transferase activities. Initial transferase assays were performed on supernatants of Sf9 cells in 6-well plates infected first or second amplified virus titers representing end-point dilutions giving optimal enzyme activities. Transferase assays of the full coding expression construct were performed by extracting washed cells in 1% Triton X-100 as described in Sorenson et al., J. Biol. Chem. 270:24166 (1995).

EXAMPLE 2

In this example, secreted GalNAc-T4 was stably expressed in Chinese Hamster Ovary cells (CHO cells). A truncated construct designed to contain amino acids 32-578 of the coding sequence of GalNAc-T4 (shown in SEQ ID NO:1 was prepared by genomic PCR using primer pairs EBHC314 (5'-AGCGGATCCGGTCAAGAAGGCTCT CAGACCTC-3', SEQ ID NO:4) and EBHC307 (5'-AGCGGATCCGACGAAAGTGCTGTTGTGCTC-3', SEQ ID NO:5). Bennett et al.(1998), supra. The product was cloned into a modified pcDNA3 vector (Invitrogen).

The pcDNA3 vector was modified to include 19 amino acids of the gamma-interferon signal sequence by directional insertion of a synthetic sequence of 91 bp coding for the interferon sequence with KpnI and BamHI flanking sites. The modified pcDNA3 vector was constructed as follows. Four synthetic oligonucleotides were synthesized: INFFOR (5'-cggggtaccggaaacgatgaaatatacaag-3', SEQ ID NO:6); INFREVA (5'-ggcggatccaggcagatcacagccaa gagaacccaaaacg-3', SEQ ID NO:7); INFREVB (5'-gcggatcccaggcagatcacagccaagagaacccaaaacg-3', SEQ ID NO:8); and INFREVC (5'-gcggatccccaggcagatcacagccaagagaacccaaaacg3', SEQ ID NO:9). Oligonucleotide primer pairs INFFOR/INFREVA, INFFOR/INFREVB and INFFOR/INFREVC were used to PCR amplify an interferon coding DNA fragment from human genomic DNA under the following conditions: 95° C. for 30 seconds, 60° C. for 5 seconds, 72° C. for 15 seconds, using Ampli-Taq (Perkin-Elmer Cetus, Conn.) and a model 480 Thermocycler (Perkin-Elmer). See FIG. 1. The use of three 3' primers spaced one base apart yields three vectors with a BamHI site positioned for any of three reading frames with respect to the signal sequence.

The GalNAc-T4 construct was cloned into pcDNA3-INF-B, and correct insertion was confirmed by sequencing. The predicted coding region of the construct is shown in FIG. 1 and SEQ ID NO:10.

CHO-K1 cells (ATCC) were transfected using 0.2 µg DNA and 5 µg lipofectamine (Invitrogen) in subconfluent 6 well plates according to the manufacturer's protocol. After 48 hours, the medium was changed and 400 µg/ml G418 was added. At 72 hours 10–20% of the wells were trypsinized and the percentage of cells expressing GalNAc-T4 was evaluated by immunocytology using an anti-GalNAc-T4 monoclonal antibody, UH6.

EXAMPLE 3

UH6 was prepared by immunizing mice with a purified GalNAc-T4 preparation that gave a single band of approximately 58,000 Daltons on SDS-PAGE Coomassie-stained gel. Balb/c mice were immunized with one subcutaneous or intraperitoneal injection of 10 ul undenatured protein in Freund's complete adjuvant, followed by two injections with Freund's incomplete adjuvant, and finally an intravenous booster without adjuvant. Eyebleeds were taken 7 days after third immunization, and the titer and specificity of anti-GalNAc-transferase antibodies was evaluated. Fusion to NS-1 and the cloning procedure was as described in White et al., Biochemistry 29:2740 (1990). The monoclonal antibody UH6 was selected for reactivity with unfixed cells and/or tissues, as well as ability to immunoprecipitate GalNAc-T4 activity. Hybridomas were selected by three criteria: i) differential reactivity in ELISA assays with purified recombinant enzymes; ii) immunocytology on Sf9 cells two days after infection with Baculovirus containing GalNAc-transferases, GalNAc-T1, -T2 or -T3; and iii) differential immunoprecipitation of active recombinant enzymes.

ELISA analysis was performed as described by White et al. (1990), supra, using purified recombinant GalNAc-T1, -T2, -T3, -T4 and AOSM, using an initial antigen concentration of 10 µg/ml.

The immunocytology assay involved washing trypsinized cells twice in PBS and airdrying the washed cells onto coverslides. Dried slides were fixed in 100% icecold acetone for 10 min, dried, and incubated with monoclonal anti-GalNAc-T4 antibody for 1 hour. After washing with PBS, slides were incubated with FITC-conjugated rabbit anti-mouse IG for 30 minutes, washed with PBS and mounted in glycerol and analyzed by microscopy.

Immunoprecipitation of recombinant human GalNAc-transferase was performed as follows. Secreted forms of human GalNAc-transferases were expressed in Sf9 cells, and media were harvested three days post-infection and used as enzyme source. Protein G Sepharose was saturated sequentially with rabbit anti-mouse IgG and monoclonal antibodies as culture supernatants. A 5% suspension of Protein G beads was added to Sf9 medium containing either GalNAc-T1, -T2, -T3 or -T4. After incubation for 1 hour at 4 degrees C, beads were washed in PBS, and resuspended in 25 mM Tris (pH 7.4), 0.25% Triton X-100. GalNAc-transferase activities were measured in the supernatants and the washed pellets using a standard reaction mixture containing 25 mM Tris (pH 7.4), 10 mM $MnCl_2$, 0.25% Triton X-100, 100 µM UDP-[$^{14}$C]-GalNAc (2,000 cpm/nmol), and 25 µg acceptor peptide substrate. UH6 selectively immunoprecipitated GalNAc-T4 activity but not GalNAc-T1, -T2 or -T3.

Western blot analysis with purified recombinant enzymes was also performed, but it proved difficult to select antibodies reactive with both the native and the denatured GalNAc-T4 enzyme. The antibody UH6 is therefore likely to be directed to a conformational epitope, and detects the native conformation of GalNAc-T4.

Based on the frequency of positive cells the residual transfectant cells from Example 2 were trypsinized and plated in 96 well plates. Two rounds of screening and cloning by limiting dilution using immunoreactivity with UH6 were performed and clones reaching over 50% positive cells were selected, and tested for level of secreted enzyme in supernatant of confluent cultures. The intensity of immunoreactivity by the cytology assay correlated in all cases with level of GalNAc-T4 enzyme activity found in spent media from clones.

EXAMPLE 4

Expression of pAcGP67-GalNAc-T4$_{506V}$sol, as described in Example 1, resulted in GalNAc-transferase activity in the culture medium of infected cells that was greater than background values obtained with uninfected controls or cells infected with the histo-blood group $O^2$ gene. Table I shows the substrate specificities of purified recombinant GalNAc-T4 and GalNAc-T2. Activities measured with the mucin derived substrates, Muc7, EA2, and Muc2 (see Table I for structures and SEQ ID NOs:19, 25 and 18, respectively), were only 2–7 fold over background values. Very low activities with a few other substrates were also observed, but for many of the "mucin-like" substrates a relative high background with Sf9 cells infected with irrelevant constructs made assessment difficult. GalNAc-T4 was expressed in High Five cells and purified to near homogeneity, however, very low endogenous activity was detected with some substrates in the same fractions when medium from cells infected with irrelevant expression constructs were used in the same purification strategy. The activities presented in Table I were obtained with purified GalNAc-T4 and -T2, and are expressed as mU/mg (the concentration of enzyme protein estimated by SDS-PAGE using BSA as standard). The highest activities with GalNAc-T4 were found from assays of Sf9 medium with the mucin peptides Muc7, EA2, and Muc2, however, the efficiencies with these substrates were considerably lower than GalNAc-T2.

EXAMPLE 5

In this example, it was demonstrated that GalNAc-T4 complements other GalNAc-transferases in complete O-glycosylation of the MUC1 tandem repeat. As seen in Table I, GalNAc-T4 showed somewhat poor activities with the MUC1 derived peptides Muc-1a, Muc-1b, and TAP24. The glycopeptide, $GalNAc_4TAP24$ (Table I and SEQ ID NO:17), was tested because it has all the acceptor sites for GalNAc-T1, -T2, and -T3 occupied, see Wandell et al., supra., and therefore is not a substrate for these enzymes. Surprisingly, a low but significant activity with this substrate was observed with purified GalNAc-T4 (Table I, Table II). Detailed analysis of the activity revealed a strikingly low apparent Km of 90 μM, although Vmax was low (Table II). Analysis of the reaction products by capillary zone electrophoresis, as described by Wandell et al., supra., indicated that a total of two moles of GalNAc were incorporated when the reaction was run to completion. Analysis of the HPLC purified product of the reaction by mass spectrometry confined the presence of six moles of GalNAc.

EXAMPLE 6

In this example, it was shown that GalNAc-T4 can O-glycosylate $Thr_{57}$ in PSGL-1. Two peptide designs of the N-terminal sequence of mature PSGL-1 were tested (Table I and SEQ ID NOs:20 and 20). In a recent study, $Thr_{57}$ of PSGL-1 was identified as the carrier site of an O-glycan required for P-selection binding. Liu et al., J. Biol. Chem. 273:7078 (1998). GalNAc-T1, -T2, and -T3, exhibited poor activities with both peptide designs, but HPLC analysis of prolonged reaction indicated that both $Thr_{44}$ and $Thr_{57}$ served as substrates, although the reaction did not go to completion for either site (Tables I and II). GalNAc-T4, in contrast, showed low activity with the PSGL-1b peptide containing both $Thr_{44}$ and $Thr_{57}$, but not with PSGL-1a without the $Thr_{57}$ site. The reaction went to completion and the apparent Km for this peptide was very low (Tables I and II). Analysis of the exhaustively glycosylated PSGL-1b peptide by mass spectrometry confined that a single GalNAc was incorporated (data not shown). A strong substrate inhibition with the negatively charged PSGL-1b peptide was observed at concentrations greater than 1 mM. The Km of purified GalNAc-T4 for UDP-GalNAc was 160 μM using the Muc7 acceptor substrate. No incorporation with UDP-Gal or UDP-GlcNAc was found using the same peptide.

EXAMPLE 7

One clone from Example 2, designated CHO/GalNAc-T4/21A1, was selected and culture medium of confluent T-flasks contained up to 0.95 mU/ml activity measured with Muc7 in the standard assay. A stable CHO clone, CHO/GaNAc-T3/H3–6, secreting 5 mU/ml GalNAc-T3 (using Muc1a acceptor substrate) has also been established using the same immunoscreening procedure, using an anti-GalNAc-T3 monoclonal antibody. GalNAc-T3 has a specific activity of 0.5 U/mg with Mucla, and GalNAc-T4 appears to have a specific activity of 0.053 U/mg with Muc7 (Table I). Thus the protein secretion level of CHO/GalNAc-T4/21A1 is approximately 20mg/L, which is comparable to, or better than, that of CHO/GalNAc-T3/H3–6, which secretes approximately 10 mg/L. Since there is no detectable endogenously secreted GalNAc-transferase activity in the medium of wild-type CHO, this enzyme source should be very valuable for studies of substrates with low efficiency. Using the method of the invention, other human glycosyltransferases (β4Gal-T2, βGal-T5, the GaM2 βGalNAc-transferase, and α3FUT5) have been expressed in CHO cells and secretion levels of 10–30 mg/L obtained.

EXAMPLE 8

Expression of $pAcGP67\text{-}GalNAc\text{-}T4_{506}$ I sol did not result in detectable GalNAc-transferase activity in the culture medium of infected cells that was greater than background values obtain with uninfected controls or cells infected with irrelevant constructs. However, the activity detectable with $pAcGP67\text{-}GalNAc\text{-}T4_{506V}sol$ directly in the culture medium of infected Sf9 cells was only a few fold over background. The expression of pAcGP67-GalNAc-$T4_{506t}sol$ as well as $pAcGP67\text{-}GalNAc\text{-}T4_{507V}sol$ and pVL-GalNAc-$T4_{516V}$ full in Sf9 cells was monitored by immunocytological reaction with UH6. Cells infected with $pAcGP67\text{-}GalNAcT4_{506V}sol$ were clearly positive, but the number of cells which were positive, and the intensity, was lower than for cells infected with pACGP67-GalNAc-$T4_{506V}sol$ and PVL-GalNAc-$T4_{506V}$full. The expression of GalNAc-$Tr_{506V}sol$ was equivalent (in terms of number of positive cells and intensity) to that previously reported for GalNAc-T1, -T2, and -T3 constructs using specific monoclonal antibodies to these enzymes. Expression of pAcGP67-GalNAc-$T4_{506t}sol$ in High Five cells followed by purification produced a catalytically active enzyme fraction with activities essentially similar to that of the GalNAc-$T4_{506V}sol$ variant.

EXAMPLE 9

Expression of pVL-GalNAc-$T4_{506V}$full in Sf9 cells did not produce significant GalNAc-transferase activities in homogenates with the same substrates as found for the secreted construct. However, this assay is influenced by a very high endogenous GalNAc-transferase background. The expression level was evaluated by immunocytology with UH6, and cells infected with the full coding construct stained stronger than those infected with the pAcGP67-GalNAc-$T4_{506V}sol$ construct. When a Triton X-100 homogenate of infected Sf9 cells was incubated with $GalNAc_4TAP24$ for 24 hours with one addition of UDP-GalNAc and extra enzyme, no incorporation was detected by MALDI-TOF of HPLC-purified product.

Each document referenced in the foregoing disclosure is incorporated by reference to the extent relevant to making or using the invention as claimed.

TABLE I

Substrate specificities of purified recombinant GalNAc-T4 and -T2

| Peptide | Sequence | GalNAc-T4 | | | GalNAc-T2 | | |
|---|---|---|---|---|---|---|---|
| | | 1 mM[a] | 0.25 mM milliunits/mg | 0.06 mM | 1 mM | 0.25 mM milliunits/mg | 0.06 mM |
| Muc1a' | AHGVTSAPDTR | 6.7 ± 1 | 2 ± 0.4 | NT[c] | 83 ± 2 | 28 ± 5 | NT |
| Muc1b' | RPAPGSTAPPA | 0.9 ± 0.8 | 0.7 ± 0.5 | NT | 582 ± 9 | 198 ± 9 | NT |
| TAP24 | TAPPAHGVTSAPDTRPAPGSTAPP | NT | 2.7 ± 0.2 | 0.8 ± 0.1 | NT | 222 ± 3 | 73 ± 2 |
| GalNAc₄TAP24 | TAPPAHGVTSAPDTRPAPGSTAPP[d] | NT | 7.1 ± 0.8 | 4.4 ± 0.1 | NT | 0.0 | 0.0 |
| Muc2 | PTTTPISTTTMVTPTPTPTC | NT | 29 ± 0.8 | 9 ± 0.5 | NT | 128 ± 5 | 169 ± 2 |
| Muc7 | CPPTPSATTPAPPSSSAPPETTAA | NT | 53 ± 2 | 21 ± 1 | NT | 396 ± 34 | 737 ± 75 |
| PSGL-1a | QATEYEYLDYDFLPEC | ND[e] | ND | ND | NT | 0.0 | 0.0 |
| PSGL-1b | Ac-QATEYEYLDYDFLPETEPPEM | NT | 1.4 ± 0.1 | 1.2 ± 0.1 | NT | 0.3 ± 0.1 | 0.3 ± 0.02 |
| HIV$_{HIB}$ gp120 | Ac-CIRIQRGPGRAFVTIGKIGNMR | ND | ND | ND | ND | ND | ND |
| VTHPGY | Ac-PFVTHPGYD | ND | ND | ND | ND | ND | ND |
| hCG-β | PRFQDSSSSKAPPPSLPSPSRLPG | ND | ND | ND | NT | 74 ± 2 | 22 ± 0.5 |
| EA2 | DSTTPAPTTK | NT | 42 ± 4 | 15 ± 0.1 | NT | 376 ± 5 | 152 ± 3 |

[a] Peptide concentration in a 50-μl assay as described.
[b] One unit of enzyme is defined as the amount of enzyme that transfers 1 μmol of GalNAc in 1 min using the standard reaction mixture as described.
[c] NT, not tested.
[d] GalNAc₄TAP24 represents the TAP24 peptide terminally glycosylated with GalNAc-T2, and GalNAc attachment site are underlined
[e] ND. not detectable, indicates that no incorporation is observed with substrate even after prolonged incubation (24 h).

TABLE II

Kinetic constants of purified recombinant GalNAc-transferases

| Substrate | Sequence | GalNAc-T1 | | GalNAc-T2 | | GalNAc-T3 | | GalNAc-T4 | |
|---|---|---|---|---|---|---|---|---|---|
| | | $K_m$ mM | $V_{max}$ nmol/min/μg | $K_m$ mM | $V_{max}$ nmol/min/μg | $K_m$ mM | $V_{max}$ nmol/min/μg | $K_m$ mM | $V_{max}$ nmol/min/μg |
| Acceptor substrate | | | | | | | | | |
| Muc7 | CPPTPSATTPAPPSSSAPPETTAA | 0.04 | 0.76 | 0.015 | 0.64 | 0.01 | 0.056 | 0.48 | 0.25 |
| EA2 | DSTTPAPPTTK | 0.07 | 0.99 | 0.85 | 1.80 | 0.46 | 0.96 | 2.19 | 0.44 |
| GalNAc₄TAP24 | TAPPAHGVTSAPDTRPAPGSTAPP[a] | NA[b] | NA | NA | NA | NA | NA | 0.09 | 0.007 |
| PSGL-1b | Ac-QATEYEYLDYDFLPETEPPEM | ND[c] | ND | ND | ND | ND | ND | 0.02 | 0.003 |
| Donor Substrate | | | | | | | | | |
| UDP-GalNAc | | 0.062[d] | | 0.010[d] | | 0.029[d] | | 0.16[e] | |

[a] GalNAc₄TAP24 represents the TAP24 peptide terminally glycosylated with GalNAc-T2, and GalNAc attachment sites are underlined (8).
[b] NA, not applicable, indicates that no incorporation is observed with substrate even after prolonged incubations (24 h).
[c] ND, not determined, indicates that although incorporation is observed $K_m$ was higher than 2 mM and therefore not analyzed due to required quantities of peptides.
[d] Data from Wandall et al. (8).
[e] Determination of $K_m$ for UDP-GalNAc was performed with saturating concentration of Muc7 as substrate. No incorporation was found with UDP-Gal or UDP-GlcNAc.
Reference 8:
Wandell et al.; J. Biol. Chem. 272:23503 (1997)

What is claimed is:

1. A method of glycosylating an MUC1 acceptor substrate, which comprises:
   glycosylating the substrate with enzymatically active N-acetylgalactosaminyltransferase T1 (GalNAc-T1), N-acetylgalactosaminyltransferase T2 (GalNAc-T2), or N-acetylgalactosaminyltransferase T3 (GalNAc-T3); and
   further glycosylating the substrate with enzymatically-active human N-acetylgalactosaminyltransferase T4 (GalNAc-T4) to glycosylate the serine position of GVTSA and the threonine position of PDTR in the substrate.

2. The method of claim 1, wherein the GalNAc-T4 has the sequence shown in SEQ ID NO:2.

3. The method of claim 1 wherein the substrate is a multimer of MUC1 tandem repeats.

4. A method of glycosylating an MUC1 acceptor substrate, which comprises:
   glycosylating the substrate with an enzymatically active N-acetylgalactosaminyltransferase capable of glycosylating MUC1 glycosylation sites that can be glycosylated by N-acetylgalactosaminyltransferase T1 (GalNAc-T1), N-acetylgalactosaminyltransferase T2 (GalNAc-T2), or N-acetylgalactosaminyltransferase T3 (GalNAc-T3); and
   further glycosylating the substrate with enzymatically-active human N-acetylgalactosaminyltransferase T4 (GalNAc-T4) to glycosylate the serine position of GVTSA and the threonine position of PDTR in the substrate.

* * * * *

UNITED STATES PATENT AND TRADEMARK OFFICE
CERTIFICATE OF CORRECTION

PATENT NO. : 6,465,220 B1
DATED : October 15, 2002
INVENTOR(S) : Helle Hassan et al.

It is certified that error appears in the above-identified patent and that said Letters Patent is hereby corrected as shown below:

<u>Title page,</u>
Item [75], Inventor's name should read -- Helle Hassan, Fredericksberg --; and "Detlef Eisenkrätzer and Jochen Gätgens" should be deleted.

<u>Column 7,</u>
Lines 39-40, the parenthetical should read: -- (Table I and SEQ ID NOs:20 and 21) --.

<u>Column 15,</u>
Line 20, delete "<u>T1</u>" and insert -- T1 --.
Line 21, delete "<u>T2</u>" and insert -- T2 --.
Line 22, delete "<u>T3</u>" and insert -- T3 --.
Line 25, delete "<u>T4</u>" and insert -- T4 --.

Signed and Sealed this

Thirteenth Day of April, 2004

JON W. DUDAS
*Acting Director of the United States Patent and Trademark Office*

SEQUENCE LISTING

<160> NUMBER OF SEQ ID NOS: 2

<210> SEQ ID NO 1
<211> LENGTH: 1737
<212> TYPE: DNA
<213> ORGANISM: Human

<400> SEQUENCE: 1

```
atggcggtga ggtggacttg ggcaggcaag acctgcctgc tgctggcgtt tttaacagtg      60
gcctatatct tcgtggagct cttggtctct acttttcatg cctccgcagg agccggccgt     120
gccagggagc tggggtcaag aaggctctca gacctccaga aaaatacgga ggatttgtct     180
```

-continued

```
cgaccgcttt ataagaagcc ccctgcagat tcccgtgcac ttggggagtg ggggaaagcc      240
agcaaactcc agctcaacga ggatgaactg aagcagcaag aagaactcat tgagagatac      300
gccatcaata tttacctcag tgacaggatt ccctgcatc acacataga ggataaaaga       360 atgtatgagt gtaagtccca gaagttcaac tataggacac ttcctaccac ctctgttatc      420
attgctttct ataacgaagc ctggtcgact ttgctccgta ccattcacag tgttttagaa      480
acttctcctg cagttctttt gaaagagatc atcttggtgg atgacttgag tgacagagtt      540
tatttgaaga cacaacttga aacttacatc agcaatcttg atagagtacg cttgattagg      600
accaataagc gagagggct ggttagggcc cgtctgattg ggccacttt cgccactggg        660 gacgtcctca ctttcctgta ttgtcactgt gagtgtaatt ccggttggct ggaaccgctt      720
ttggaaagga ttgggagata tgaaacagca gttgtgtgtc ctgttataga cacaattgat      780
tggaatactt tgaattcta tatgcagata ggggagccca tgattggtgg gtttgactgg      840
cgtttaacat tcagtggca ttctgtcccc aaacaggaaa gggacaggcg gatatcaaga      900
attgacccca tcagatcacc taccatggct ggaggactgt ttgctgtcag caagaaatat      960
tttcagtacc ttgaacgta tgacacagga atggaagtgt ggggaggtga aaaccttgag      1020
ctgtctttta gggtgtggca gtgtggtggc aaattggaga tccacccgtg ttcccacgtg      1080
ggccatgtgt tccccaagcg ggcaccatat gctcgcccca atttcctaca gaatactgct      1140
cgggcagcag aagtttggat ggatgaatac aaagagcact tctacaatag aaaccctcca      1200
gcaagaaaag aagcttatgg tgatatttct gaaagaaaat tactacgaga gcggttgaga      1260
tgcaagagct ttgactggta tttgaaaaac gtttttccta atttacatgt tccagaggat      1320
agaccaggct ggcatggggc tattcgcagt agagggatct cgtctgaatg tttagattat      1380
aattctcctg acaacaaccc cacaggtgct aacctttcac tgtttggatg ccatggtcaa      1440
ggaggcaatc aattctttga atatacttca acaaagaaa taaggtttaa ttctgtgaca      1500
gagttatgtg cagaggtacc tgagcaaaaa aattatgtgg gaatgcaaaa ttgtcccaaa      1560
gatgggttcc ctgtaccagc aaacattatt tggcatttta agaagatgg aactatttt       1620 cacccacact caggactgtg tcttagtgct tatcggacac cggagggccg acctgatgta      1680
caaatgagaa cttgtgatgc tctagataaa atcaaattt ggagttttga gaaatag         1737
```

<210> SEQ ID NO 2
<211> LENGTH: 578
<212> TYPE: PRT
<213> ORGANISM: Human

<400> SEQUENCE: 2

```
Met Ala Val Arg Trp Thr Trp Ala Gly Lys Thr Cys Leu Leu Leu Ala
  1               5                  10                  15

Phe Leu Thr Val Ala Tyr Ile Phe Val Glu Leu Leu Val Ser Thr Phe
                 20                  25                  30

His Ala Ser Ala Gly Ala Gly Arg Ala Arg Glu Leu Gly Ser Arg Arg
             35                  40                  45

Leu Ser Asp Leu Gln Lys Asn Thr Glu Asp Leu Ser Arg Pro Leu Tyr
         50                  55                  60

Lys Lys Pro Pro Ala Asp Ser Arg Ala Leu Gly Glu Trp Gly Lys Ala
 65                  70                  75                  80

Ser Lys Leu Gln Leu Asn Glu Asp Glu Leu Lys Gln Gln Glu Glu Leu
                 85                  90                  95
```

```
Ile Glu Arg Tyr Ala Ile Asn Ile Tyr Leu Ser Asp Arg Ile Ser Leu
            100                 105                 110
His Arg His Ile Glu Asp Lys Arg Met Tyr Glu Cys Lys Ser Gln Lys
            115                 120                 125
Phe Asn Tyr Arg Thr Leu Pro Thr Thr Ser Val Ile Ile Ala Phe Tyr
            130                 135                 140
Asn Glu Ala Trp Ser Thr Leu Leu Arg Thr Ile His Ser Val Leu Glu
145                 150                 155                 160
Thr Ser Pro Ala Val Leu Leu Lys Glu Ile Ile Leu Val Asp Asp Leu
                165                 170                 175
Ser Asp Arg Val Tyr Leu Lys Thr Gln Leu Glu Thr Tyr Ile Ser Asn
                180                 185                 190
Leu Asp Arg Val Arg Leu Ile Arg Thr Asn Lys Arg Glu Gly Leu Val
            195                 200                 205
Arg Ala Arg Leu Ile Gly Ala Thr Phe Ala Thr Gly Asp Val Leu Thr
            210                 215                 220
Phe Leu Tyr Cys His Cys Glu Cys Asn Ser Gly Trp Leu Glu Pro Leu
225                 230                 235                 240
Leu Glu Arg Ile Gly Arg Tyr Glu Thr Ala Val Val Cys Pro Val Ile
                245                 250                 255
Asp Thr Ile Asp Trp Asn Thr Phe Glu Phe Tyr Met Gln Ile Gly Glu
            260                 265                 270
Pro Met Ile Gly Gly Phe Asp Trp Arg Leu Thr Phe Gln Trp His Ser
            275                 280                 285
Val Pro Lys Gln Glu Arg Asp Arg Arg Ile Ser Arg Ile Asp Pro Ile
            290                 295                 300
Arg Ser Pro Thr Met Ala Gly Gly Leu Phe Ala Val Ser Lys Lys Tyr
305                 310                 315                 320
Phe Gln Tyr Leu Gly Thr Tyr Asp Thr Gly Met Glu Val Trp Gly Gly
                325                 330                 335
Glu Asn Leu Glu Leu Ser Phe Arg Val Trp Gln Cys Gly Gly Lys Leu
            340                 345                 350
Glu Ile His Pro Cys Ser His Val Gly His Val Phe Pro Lys Arg Ala
            355                 360                 365
Pro Tyr Ala Arg Pro Asn Phe Leu Gln Asn Thr Ala Arg Ala Ala Glu
            370                 375                 380
Val Trp Met Asp Glu Tyr Lys Glu His Phe Tyr Asn Arg Asn Pro Pro
385                 390                 395                 400
Ala Arg Lys Glu Ala Tyr Gly Asp Ile Ser Glu Arg Lys Leu Leu Arg
                405                 410                 415
Glu Arg Leu Arg Cys Lys Ser Phe Asp Trp Tyr Leu Lys Asn Val Phe
            420                 425                 430
Pro Asn Leu His Val Pro Glu Asp Arg Pro Gly Trp His Gly Ala Ile
            435                 440                 445
Arg Ser Arg Gly Ile Ser Ser Glu Cys Leu Asp Tyr Asn Ser Pro Asp
            450                 455                 460
Asn Asn Pro Thr Gly Ala Asn Leu Ser Leu Phe Gly Cys His Gly Gln
465                 470                 475                 480
Gly Gly Asn Gln Phe Phe Glu Tyr Thr Ser Asn Lys Glu Ile Arg Phe
                485                 490                 495
Asn Ser Val Thr Glu Leu Cys Ala Glu Val Pro Glu Gln Lys Asn Tyr
            500                 505                 510
Val Gly Met Gln Asn Cys Pro Lys Asp Gly Phe Pro Val Pro Ala Asn
```

```
                  515                 520                    525
Ile Ile Trp His Phe Lys Glu Asp Gly Thr Ile Phe His Pro His Ser
    530                 535                 540

Gly Leu Cys Leu Ser Ala Tyr Arg Thr Pro Glu Gly Arg Pro Asp Val
545                 550                 555                 560

Gln Met Arg Thr Cys Asp Ala Leu Asp Lys Asn Gln Ile Trp Ser Phe
                565                 570                 575

Glu Lys
```